United States Patent [19]

Tinder et al.

[11] Patent Number: 5,658,144
[45] Date of Patent: Aug. 19, 1997

[54] DENTAL SYRINGE

[75] Inventors: Cameron L. Tinder, 15926 22nd Ct., Veradale, Wash. 99037; Charmaine Bianca Jones, Lewiston, Id.

[73] Assignee: Cameron L. Tinder, Clarkston, Wash.

[21] Appl. No.: 415,233

[22] Filed: Mar. 29, 1995

[51] Int. Cl.⁶ .................................................. A61C 17/02
[52] U.S. Cl. ........................ 433/80; 433/85; 433/88
[58] Field of Search .................................. 433/80, 84, 85, 433/100, 88; 601/162, 165, 169; 604/24, 236, 249, 275

[56] References Cited

U.S. PATENT DOCUMENTS

| | | | |
|---|---|---|---|
| D. 316,600 | 4/1991 | Austin, Jr. et al. | D24/14 |
| 2,112,629 | 3/1938 | Lloyd | 604/249 |
| 3,698,088 | 10/1972 | Austin, Jr. | |
| 3,874,083 | 4/1975 | Buckley | 433/80 |
| 4,026,025 | 5/1977 | Hunt | 433/80 |
| 4,249,899 | 2/1981 | Davis | 433/80 |
| 4,975,054 | 12/1990 | Esrock | 433/80 |
| 5,045,055 | 9/1991 | Gonser et al. | 604/33 |
| 5,199,871 | 4/1993 | Young | 433/80 |

*Primary Examiner*—Cary E. O'Connor
*Attorney, Agent, or Firm*—Wells, St.John, Roberts, Gregory & Matkin, P.S.

[57] ABSTRACT

A dental syringe for delivering three discrete fluids, such as water, medicine, and air. The syringe includes a housing having a plurality of fluid intake passageways and an exhaust passageway, and wherein the fluid intake passageways are connected in fluid flowing relation relative to the exhaust passageway, and a plurality of selectively controllable valves are borne by the housing and operable to meter fluid flow from the individual intake passageways.

29 Claims, 5 Drawing Sheets

FIG 6

Fig. 7

DENTAL SYRINGE

TECHNICAL FIELD

The present invention relates in general to an apparatus for delivering discrete fluids to an object of interest and more specifically to a dental syringe which may be utilized in the treatment of various dental anomalies and malocclusions and which is operable to deliver discrete fluids or mixtures thereof to the oral cavity of a patient.

BACKGROUND OF THE INVENTION

The prior art is replete with numerous examples of assorted dental syringes and other assemblies which have been employed to deliver fluids such as air, water and mixtures of same into the oral cavity of a patient. These assemblies are exemplified by U.S. Pat. No. 5,199,871 to Young and include a pair of valve assemblies which are connected in fluid flowing relation relative to a source of air and water, respectively, and which can be selectively controlled by a dental practitioner to facilitate the delivery of air, water, or a combination of air and water into the oral cavity of a patient.

As the techniques for the treatment of various dental anomalies have improved over time, dental practitioners have sought new and innovative methods for the delivery of treatment fluids, such as antiseptics, mouthwashes, antibiotics, and other fluidic materials to the oral cavity of a patient. Some of these methods have included field expedient methods such as the use of disposable cups or other containers from which the patient drinks or from which the materials are selectively dispensed by the practitioner, or alternatively, the practitioner employs conventional disposable syringes which may be utilized to direct a stream of fluid to a discrete location of concern to the practitioner.

While these field expedient methods have operated with varying degrees of success, they have several shortcomings which have detracted from their usefulness. More specifically, such methods have increased the difficulty in delivering these fluids to the area of concern or object of interest in the oral cavity, and further, each method has unduly multiplied the number of materials used in treatment process in view of the requirement that the practitioner maintain a supply of the specific containers or syringes readily available during the treatment process. Still further, the use of these field expedient modalities further increases the likelihood that the fluids may be contaminated by bacteria or other material as a result of the contamination of these objects during storage or while being employed in the treatment process.

SUMMARY OF THE INVENTION

It is an object of the present invention to provide an improved dental syringe for selectively delivering discrete fluids to the oral cavity of a patient. More specifically, it is an object of the present invention is to provide a dental syringe for delivering water, solutions containing water, liquid medicaments, and drying air to the oral cavity of a patient.

With regard to one form of the invention, it is another object of the present invention is to provide a dental syringe which includes a main body having first, second, and third fluid intake passageways, and an exhaust passageway, and wherein the first and second fluid intake passageways are serially connected in fluid discharging relation relative to the exhaust passageway, and the third passageway is individually connected in fluid discharging relation relative to the exhaust passageway.

With regard to one form of the invention, it is another object of the present invention is to provide a dental syringe which includes a plurality of selectively controllable valves which are borne by the housing and which individually control the flow of each of the fluids from the respective fluid intake passageways to the exhaust passageway.

With regard to one form of the invention, it is another object of the present invention is to provide a dental syringe which includes a sleeve which is telescopingly received in each of the fluid intake passageways, and wherein the sleeve further defines a primary passageway and a secondary passageway which is connected in fluid flowing relation relative thereto.

With regard to one form of the invention, it is another object of the present invention is to provide a dental syringe which includes a plunger which is received in the primary passageway and which operates in combination with a sealing member which moves along a given path of travel from a first, closed or occluding position, to a second, open or non-occluding position, and wherein the sealing member when disposed in the second position, facilitates the flow of fluid from the respective fluid intake passageway to the exhaust passageway.

With regard to one form of the invention, it is another object of the present invention is to provide a dental syringe which is easy to assemble and place into operation and which is further readily accessed for purposes of maintenance, modification and the like.

With regard to one form of the invention, it is another object of the present invention is to provide a dental syringe which is characterized by ease of utilization, simplicity of construction, and which further can be manufactured, sold and maintained at a relatively nominal cost.

These and other objects and advantages are achieved in a dental syringe for delivering discrete fluids which includes a housing having a plurality of fluid intake passageways and an exhaust passageway, and wherein the fluid intake passageways are connected in fluid discharging relation relative to the exhaust passageway; and a plurality of selectively controllable valves are borne by the housing and are individually operable to selectively control fluid flow from the individual fluid intake passageways to the exhaust passageway, respectively.

BRIEF DESCRIPTION OF THE DRAWINGS

Preferred embodiments of the invention are described below with reference to the accompanying drawings, which are briefly described below.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
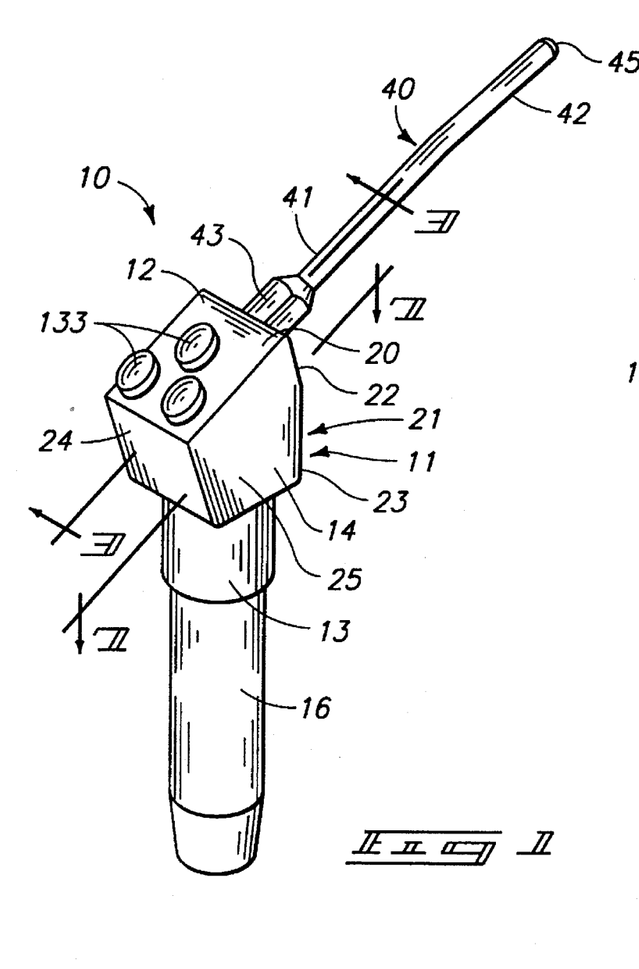
FIG. 1 is a perspective, environmental view of the apparatus of the present invention.

The apparatus for selectively delivering discrete fluids to an object of interest is generally shown by the numeral 10 in FIG. 1. As illustrated therein, the apparatus 10 includes a housing or main body 11 which has a first end 12 and a distal or second end 13. The housing has an exterior facing surface 14 and an opposite interior facing surface 15 which defines various fluid passageways which will be discussed in greater detail hereinafter. The apparatus 10 further includes a handle 16 which screw-threadably engages the second end of the housing and provides a means for a practitioner to grasp the apparatus 10 and position it in any desired orientation. The handle further provides a passageway 17, which can receive several flexible conduits, and which in turn are individually connected in fluid flowing relation to discrete supplies of fluids which are to be dispensed.

Figure 3:
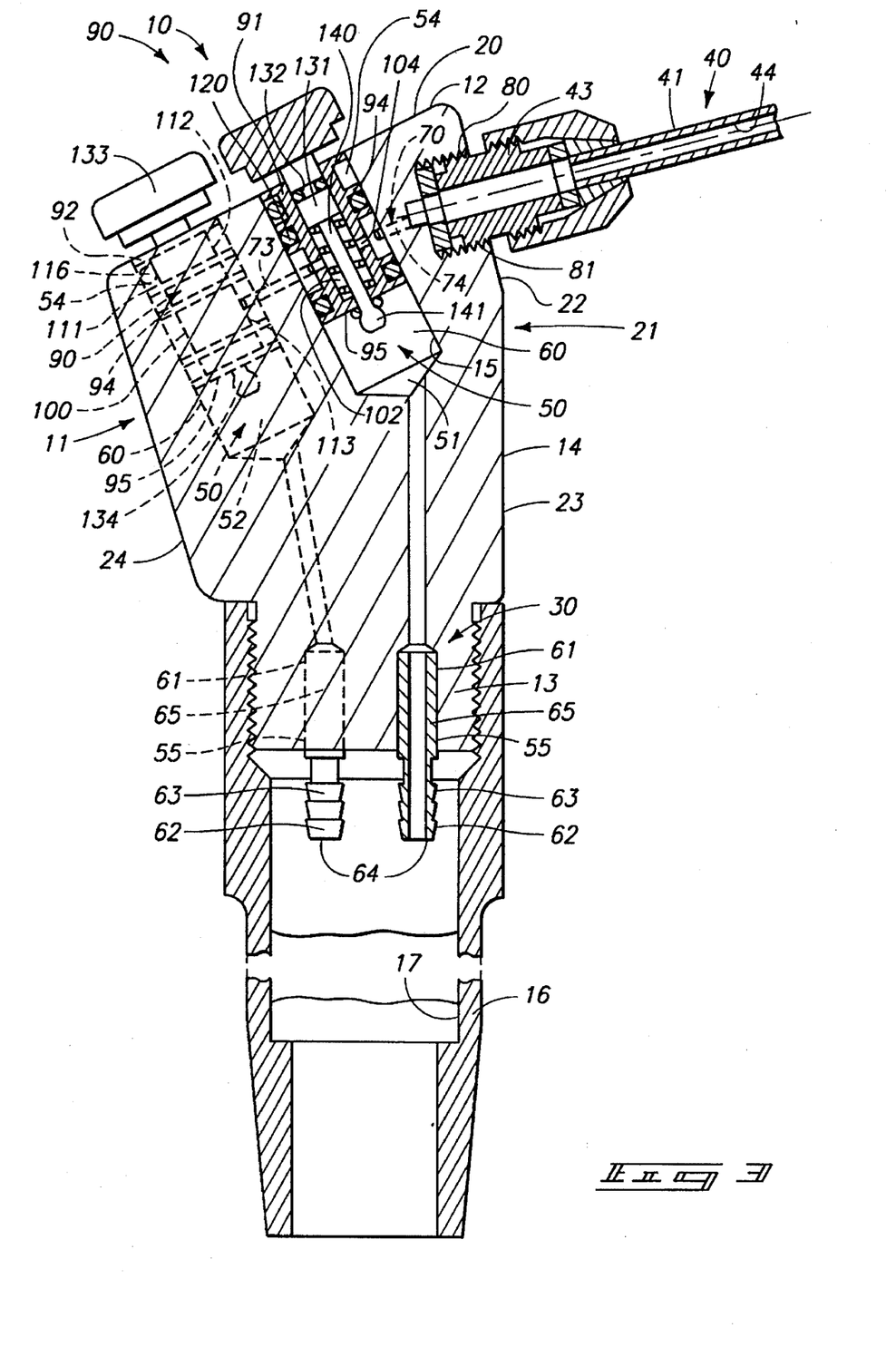
FIG. 3 is a fragmentary, longitudinal, vertical, sectional view taken from a position along line 3—3 of FIG. 1.
Figure 4:
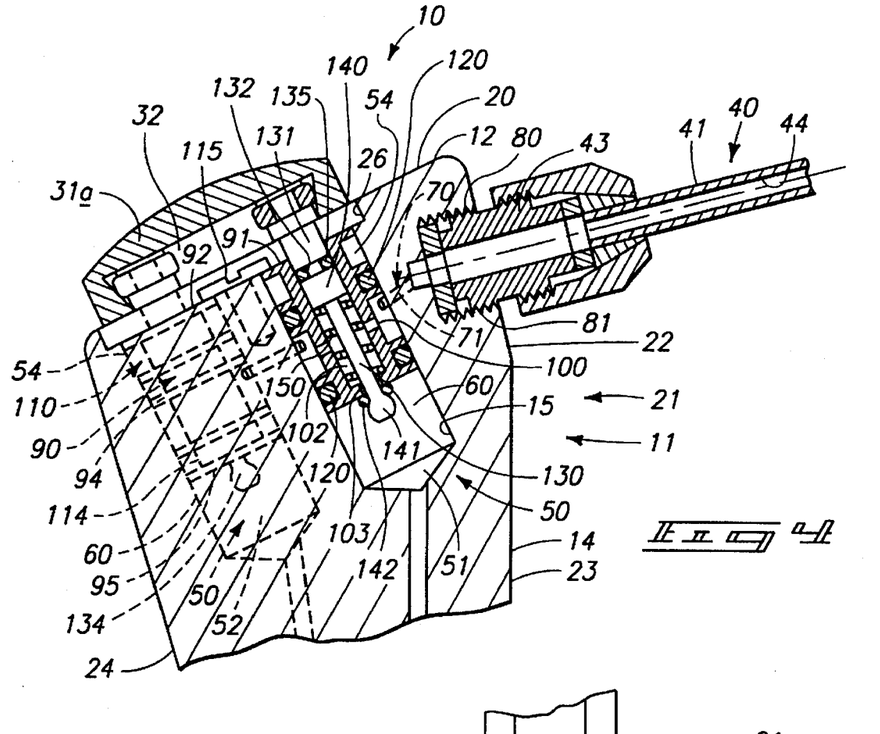
FIG. 4 is a fragmentary, longitudinal, vertical, sectional view taken from a position along line 4—4 of FIG. 2, and showing one form of the invention which includes a substantially rigid cap.
Figure 5:
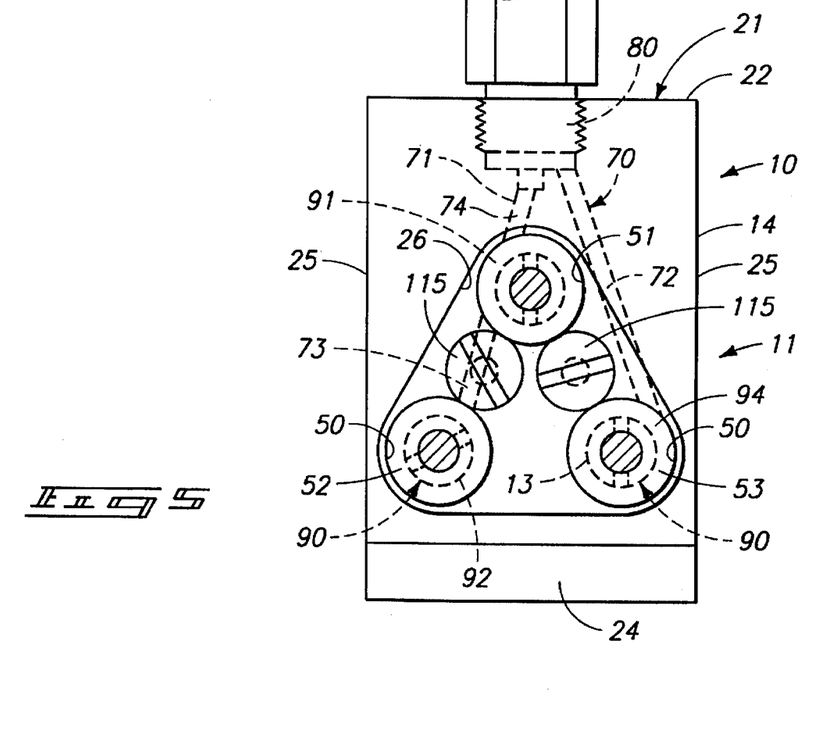
FIG. 5 is a fragmentary, transverse, sectional view taken from a position along line 5—5 of FIG. 2.
Figure 6:
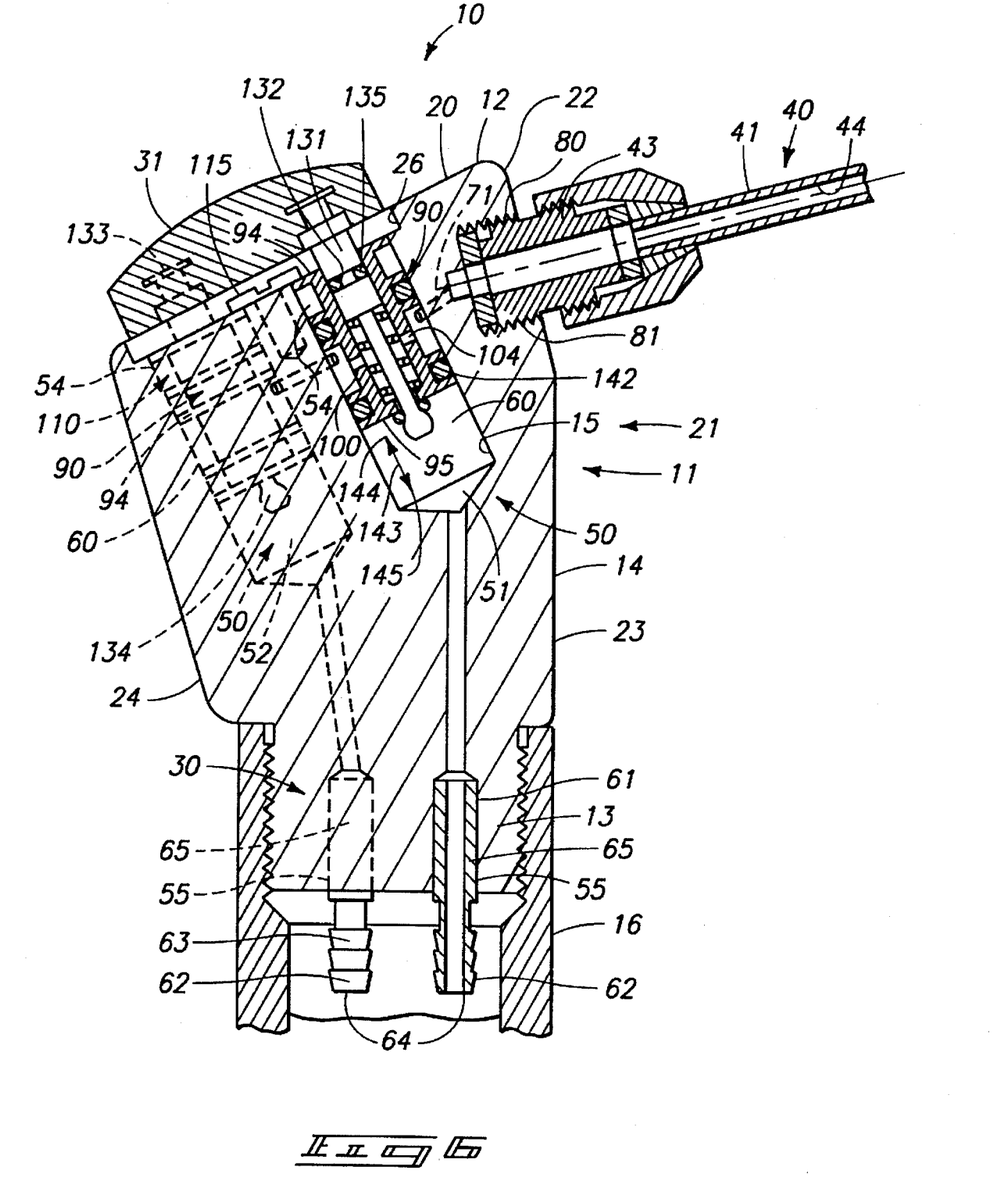
FIG. 6 is a second somewhat enlarged fragmentary, longitudinal, vertical, sectional view taken from a position parallel to line 4—4 of FIG. 2, and showing a second form of the invention which includes a flexible cap, or membrane.

As best seen by reference to FIG. 3, the housing or main body 11 includes an angulated, top, or exterior facing surface 20; a forwardly facing surface 21 which has a first portion 22, and a second portion 23, which is disposed in angulated relation relative thereto; an angulated rear wall 24; and a pair of sidewalls 25 which are disposed in substantially parallel, spaced relation one-to-the-other. The housing further includes a base portion 30, which is of reduced dimensions in relative comparison to the main body 11 and which threadably mates with the handle 16. As best seen in FIG. 6, a flexible membrane or cap 31 releasably mates with the housing 11. Further and as shown in FIG. 4, in an alternate form, a substantially rigid cap 31A releasably mates with the housing. The membrane defines a cavity 32 which encloses several engagement members which will be discussed in greater detail hereinafter.

As best illustrated in FIG. 1, the apparatus 10 of the subject invention includes an angulated delivery conduit which is generally indicated by the numeral 40 and which is operable to transport the individual discrete fluids, or mixtures thereof, into the oral cavity of a patient. This angulated conduit is of conventional design. The conduit includes a first end 41 and an opposite second end 42. The first end is operable to matingly interfit with a threaded connector 43 of conventional design. The threaded connector threadably mates in fluid flowing relation relative to the main body 11. In view of the conventional nature of this threaded connector, it is not discussed in any further detail herein. The angulated conduit defines a fluid passageway 44 which terminates in a discharge orifice 45 at the distal, or second end 42.

The interior facing surface 15 defines a plurality of fluid intake passageways which are generally indicated by the numeral 50. These fluid intake passageways include first, second and third intake passageways 51, 52, and 53, respectively, and which are best seen by reference to FIGS. 3 and 4. As earlier discussed, the individual fluid intake passageways are disposed in fluid flowing relationship relative to discrete supplies of fluid (not shown), and which may be selectively delivered by a practitioner into the oral cavity of a patient for purposes of treating various dental conditions. Each of the several fluid intake passageways have a first end 54, and an opposite distal, or second end 55. As best seen by reference to FIG. 3, the individual fluid intake passageways have a proximal or first portion 60 and a distal, or second portion 61. It should be understood that the second portion has a predetermined diametral dimension and matingly receives in the manner of a friction-fit individual hose fittings 62 of conventional design. Each of the hose fittings has a barbed exterior surface 63 which is located on the first end 64. Further, each of the hose fittings has an opposite, second end 65 which is received in the second portion 61.

Figure 7:
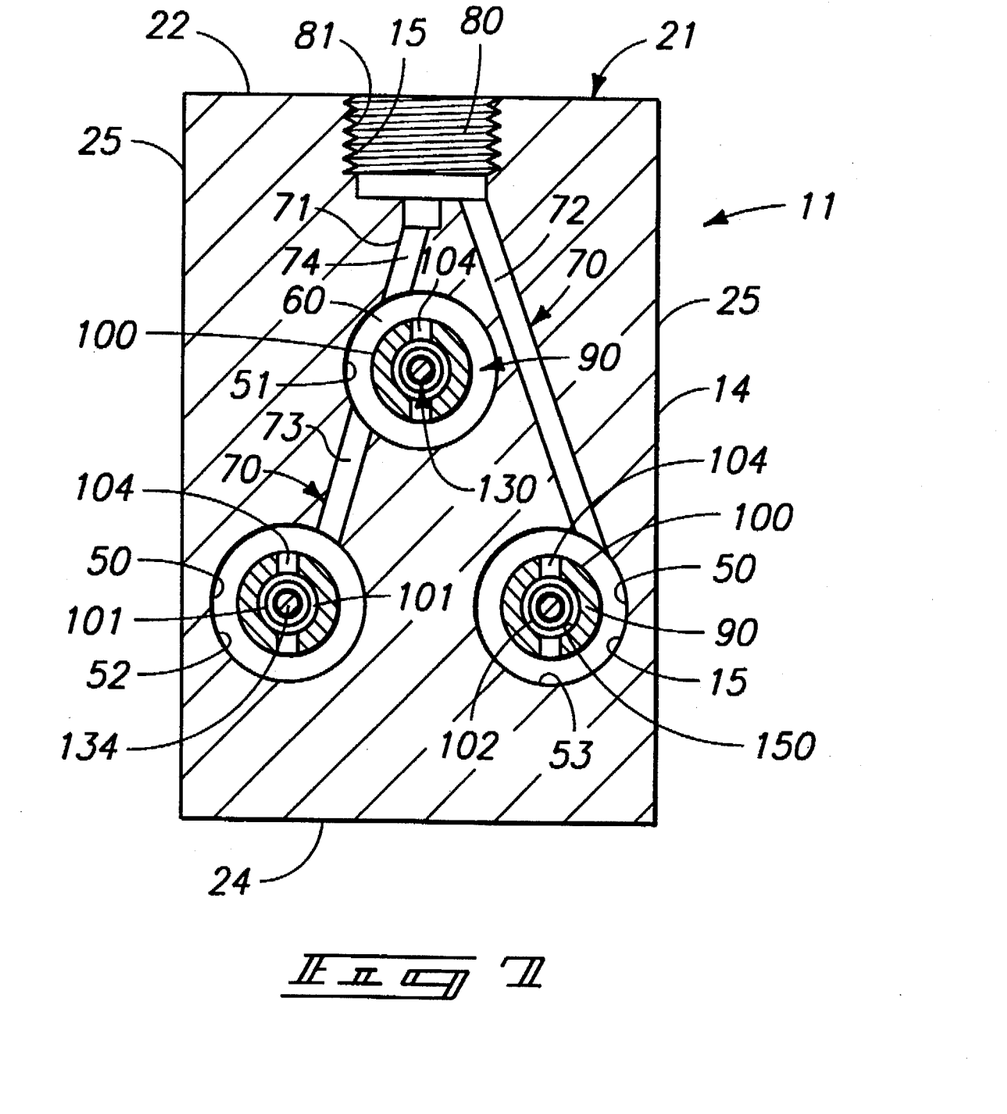
FIG. 7 is a fragmentary, transverse, sectional view which is taken from a position along line 7—7 of FIG. 1.

As best seen by reference to FIGS. 3 and 7, the main body or housing 11 defines a pair of connecting passageways 70. As shown, these include a first connecting passageway 71, and a second connecting passageway 72. As best seen by reference to FIG. 7, the first connecting passageway has a first portion 73 which connects, in fluid flowing relation, the first intake passageway 51 with the second intake passageway 52. Further, the second portion 74 connects the first intake passageway 51 with the exhaust passageway which is generally designated by the numeral 80. As best seen in FIG. 7, the exhaust passageway 80 is defined by the interior facing surface 15 and further has a plurality of threads 81 formed in the interior facing wall. These individual threads matingly engage the threaded connector 43 which was discussed earlier.

The apparatus 10 of the present invention includes individual valves 90. The valves 90 are designated as first, second and third valves 91, 92 and 93, respectively. The individual valves are positioned in fluid metering or dispensing relation relative to the individual fluid intake passageways 51, 52, and 53, respectively. In this regard, the individual valves 91, 92 and 93, respectively, include a sleeve 94. The sleeve 94 has a substantially cylindrically shaped main body 95 which has an exterior facing surface 100, and an opposite, interior facing surface 101 which defines a primary passageway 102. The primary passageway is substantially uniform in its inside diametral dimension for the majority of its length except for a reduced diametral portion which is generally designated by the numeral 103. Further, and as best seen by reference to FIG. 3, a secondary passageway 104 is disposed in fluid flowing relation relative to the primary passageway, and extends generally radially outwardly relative to the primary passageway which is oriented substantially along the longitudinal axis of the main body 95. The sleeve further includes a support member, not shown, which extends radially inwardly relative to the primary passageway and which supports a shaft which will be discussed in greater detail hereinafter.

As best seen by reference to FIGS. 3 and 4, a plurality of circumscribing grooves 110 are formed in the main body 95 of the sleeve 94. The plurality of circumscribing grooves includes first, second, third and fourth grooves 111, 112, 113, and 114, respectively. As illustrated in FIG. 3, a pair of O-rings 120, of conventional design, are individually received in the second and fourth grooves 112, and 114, respectively, and thereby provides a means for fluid sealably securing the sleeve in interfitted mating relation relative to the respective intake passageways 51 through 53, respectively. Several threaded fasteners 115 threadably mate with the housing 11 and operate to secure the individual valves 90 in the respective fluid intake passageways 50. In addition, and as seen in FIG. 3, individual pins 116 are operable to engage the valve body in a fashion which will secure it in a predetermined position relative to the respective intake passageway. The valve body will be discussed in the paragraphs which follow.

Figure 2:
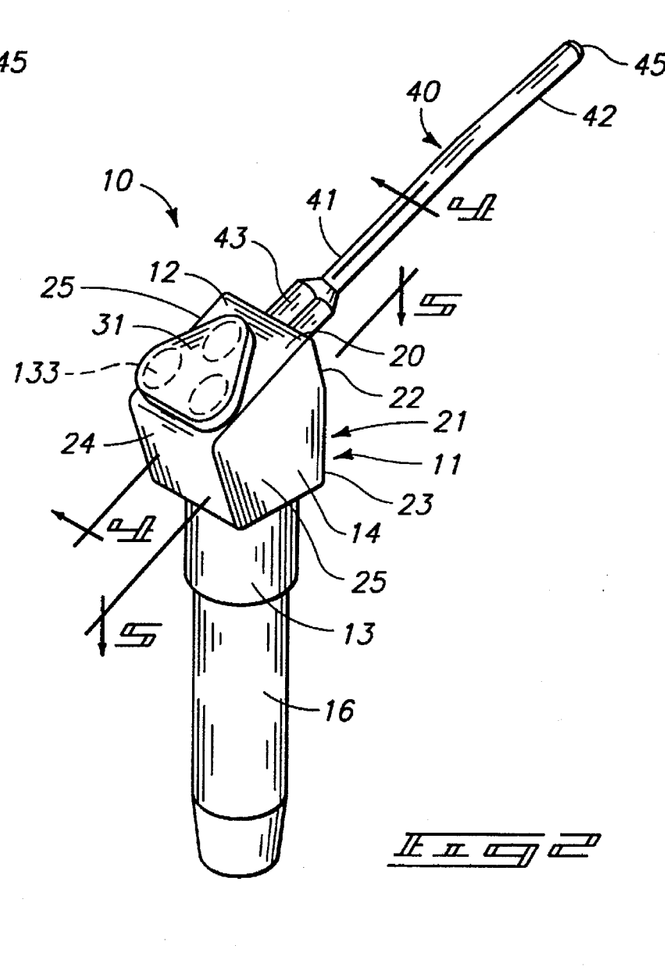
FIG. 2 is a perspective, environmental view of a second form of the apparatus of the present invention.

As best illustrated in FIGS. 3 and 4, a valve body is generally indicated by the numeral 130, and includes a plunger 131 which has formed therein a substantially circumscribing groove 132. Further, the valve body includes a shaft 134, which is oriented substantially centrally relative to the primary passageway 102, by means of the support member (not shown), and which was discussed earlier. The plunger further includes an engagement member 133, which is made integral with the plunger, and which may be forcibly engaged by the finger of a dental technician (not shown). In an alternative form of the invention shown in FIG. 2, the flexible membrane 31 is disposed in covering relation relative to the individual engagement members. In this form of the invention, force applied to the membrane causes it to distort, thereby allowing the force to be transmitted directly to the respective engagement members. Additionally, an O-ring 135 is received in the circumscribing groove 132. The shaft 134 further has a proximal end 140, and an opposite, distal end 141. A sealing member 142, is releasably mounted on the distal end 141 of the shaft, and is operable to selectively occlude the primary passageway 102. In this regard, it should be understood that the valve body 130 is operable to move along a substantially linearly oriented, and reciprocal path of travel 143 from a first, or occluding position 144, to a second, displaced, or fluid flowing position 145. Still further, the valve body includes a biasing member 150 which is received about the shaft, and which is operable to coact with the valve body and the shaft, thereby urging the valve body and more specifically the sealing member to move along the path of travel 143 in the direction of the first position. As noted above, when the valve body is disposed in the first position, the sealing member 142 is oriented in occluding relation relative to the primary passageway, thereby preventing fluid from moving from the respective intake passageways 51, 52, and 53 into the exhaust passageway 80.

OPERATION

The operation of the described embodiment of the present invention is believed to readily apparent and is briefly summarized at this point.

The dental syringe apparatus 10 for delivering discrete fluids includes a housing 11 having a plurality of fluid intake passageways 51, 52, and 53; and an exhaust passageway 80, respectively. As best seen by reference to FIG. 6, the fluid intake passageways are connected in fluid flowing relation relative to the exhaust passageway 80. Further, the apparatus 10 includes a plurality of selectively controllable valves 90 which are borne by the housing 10 and which are operable to meter the flow of the fluid from the individual fluid intake passageways. In this regard, it should be understood that individual sources of fluid (not shown) would be connected in fluid flowing relation relative to the individual hose fittings 62 which are shown most clearly in FIG. 3. The fluids which are dispensed may include air, water, medicaments of all sorts, and any other fluids which could be employed for dental hygiene or for treatment of various dental conditions. As best seen by reference to FIG. 6, the first, second and third fluid intake passageways are connected in fluid flowing relation relative to the exhaust passageway 80 by means of first and second connecting passageways 71 and 72 respectively. More specifically, the first and second fluid intake passageways are serially connected in fluid discharging relation relative to the exhaust passageway; and the third fluid intake passageway is individually connected in fluid discharging relation relative to the exhaust passageway.

A sleeve 94 is telescopingly received in sealing relationship in each of the fluid intake passageways 51, 52 and 53 respectively. Each of the sleeves has an exterior facing surface 100, and an opposite, interior facing surface 101, and wherein the interior facing surface defines a primary passageway 102 which is oriented along the longitudinal axis of the sleeve. Further, a secondary passageway 104 is formed in each of the sleeves and is disposed in fluid flowing relation relative to the primary passageway and the respective connecting passageways. As noted earlier, a plunger 131 is borne by the respective sleeves and is moveable along the primary passageway. The valve body further includes a shaft 134 having a distal end 141. The plunger is moveable along a given path to travel 143 from a first position 144, to a second position 145. A biasing member 150 is received about the shaft and coacts with the sleeve and the shaft. The biasing member urges the plunger and the sealing member 142 in the direction of the first position. Further, the sealing member 142 is borne on the distal end of each of the shafts. Seal 142 is operable to selectively occlude the individual primary passageways 102 when the individual plungers, and the associated shafts are positioned in the first position. Seal 142 is displaced a predetermined distance from the sleeve when the plunger and shaft are disposed in the second position. This allows the flow of fluid from the respective intake passageways to the exhaust passageway by way of the secondary passageways 104.

The apparatus 10 provides a convenient means by which a dental practitioner (not shown) may hand-manipulate or otherwise orient the apparatus 10 in a fashion whereby selective fluids, or mixtures thereof, may be delivered into the oral cavity of a patient in a fashion not possible heretofore. In particular, the apparatus 10 provides a means for receiving the respective fluids in a hand-manipulatable housing 11 which includes a plurality of fluid intake passageways 51, 52, and 53; selectively delivering the individual fluids to an exhaust passageway 80; directing the fluids from the exhaust passageway towards the object of interest; and providing a means for mixing the individual fluids while they move along the exhaust passageway for delivery at the object of interest.

Therefore, the apparatus 10 of the subject invention can be utilized for the delivery of selected fluids into the oral cavity of a patient without further modifications thereto. In addition, the present invention may be used in all manner of dental treatment regimens, and provides flexibility with respect to the delivery of any number of selected fluids or mixtures thereof into the oral cavity of a patient. Further, the apparatus is easy to employ, is simple to maintain, and further can be manufactured at a nominal price when compared with other prior art devices which are utilized for substantially identical purposes.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A syringe primarily for dental use for controllably and independently delivering water, drying gas, and a medicament to the mouth of a patient, comprising:

a housing having a water intake passageway, a gas intake passageway, and a medicament intake passageway;

said housing also having an exhaust passageway; said intake passageways and said exhaust passageway being connected together in fluid flowing relation;

a dispensing conduit connected to receive fluids from the exhaust passageway;

a water valve for controlling water flow from the water intake passageway to the exhaust passageway;

a gas valve for controlling gas flow from the gas intake passageway to the exhaust passageway;

a medicament valve for controlling medicament flow from the medicament intake passageway to the exhaust passageway;

a handle connected to the housing.

2. A dental syringe according to claim 1 and further comprising a covering which extends over engagement members forming part of said valves.

3. A dental syringe according to claim 1 and wherein the housing further defines first and second connecting passageways, and wherein the first passageway serially connects two of the three fluid intake passageways in fluid flowing relation relative to the exhaust passageway, and the second connecting passageway connects the remaining fluid intake passageway in fluid flowing relation relative to the exhaust passageway.

4. A dental syringe for delivering discrete fluids comprising:

a housing defining three fluid intake passageways, and an exhaust passageway which are connected together in fluid flowing relation;

a dispensing conduit borne by the housing and disposed in fluid receiving relation relative to the exhaust passageway;

a handle borne by the housing; and three valves borne by the housing and mounted in individual fluid metering relation relative to each of the fluid intake passageways.

5. A dental syringe as claimed in claim 4, and wherein the housing further defines first and second connecting passageways, and wherein the first passageway serially connects two of the three fluid intake passageways in fluid flowing relation relative to the exhaust passageway, and the second connecting passageway connects the remaining fluid intake passageway in fluid flowing relation relative to the exhaust passageway.

6. A dental syringe as claimed in claim 4, and wherein the housing further defines first and second connecting passageways, and wherein the first passageway serially connects two of the three fluid intake passageways in fluid flowing relation relative to the exhaust passageway, and the second connecting passageway connects the remaining fluid intake passageway in fluid flowing relation relative to the exhaust passageway; and wherein the individual valves each have a valve body which is received in the individual fluid intake passageways and which is selectively moveable along a given path of travel from an occluding, fluid impeding position, to an open position which facilitates fluid flow.

7. A dental syringe as claimed in claim 6, and wherein the valve body includes a plunger and a shaft which mounts a sealing member, and wherein the plunger further includes a force engagement surface, and wherein a biasing member is received about the shaft and coacts with the sleeve, plunger and shaft, thereby urging the plunger and the sealing member to move in the direction of the first position.

8. A dental syringe for selectively delivering discrete fluids to an object of interest, comprising:

a housing having first, second, and third fluid intake passageways, and an exhaust passageway, and wherein the first and second fluid intake passageways are serially connected in fluid discharging relation relative to the exhaust passageway, and the third passageway is individually connected in fluid discharging relation relative to the exhaust passageway; and a selectively controllable valve body mounted in each of the fluid intake passageways and moveable along a given path of travel from a first normally closed position wherein fluid movement is impeded from the individual fluid intake passageways to the exhaust passageway, to a second position wherein the valve body facilitates movement of the fluid from the individual fluid intake passages to the exhaust passage.

9. A dental syringe as claimed in claim 8, and wherein the individual fluid intake passages have a given length and diametral dimension, and opposite first and second ends, and wherein a first connecting passageway serial connects the first and second fluid intake passageways in fluid discharging relation relative to the exhaust passageway, and wherein the first connecting passageway has a first and second portion, and wherein the first portion connects in fluid flowing relation the first and second fluid intake passageways, and the second portion connects the second fluid intake passageway to the exhaust passageway.

10. A dental syringe as claimed in claim 9, and wherein the third fluid intake passageway is connected in fluid flowing relation relative to the exhaust passageway by means of a second connecting passageway, and wherein the first and second connecting passageways are oriented in intermediate relation relative to the first and second ends of the individual fluid intake passageways.

11. A dental syringe as claimed in claim 10, and wherein the valve body includes a sleeve which is telescopingly received in each of the fluid intake passages, and wherein the sleeve has a main body with opposite first and second ends and further defines a primary passageway which is oriented along the longitudinal axis of the main body, and a secondary passageway which is disposed in substantially radially extending relation relative to the primary passageway, and wherein the valve body further includes a plunger assembly which is disposed in reciprocally moveable relation relative to the primary passageway, and wherein a seal is received about the main body and is operable to engage the housing.

12. A dental syringe as claimed in claim 11, and wherein the plunger assembly has a plunger portion which is slidably received in the primary passageway, and wherein the valve body further includes a shaft which is born by the sleeve, and which has a proximal end which coacts with the plunger portion, and an opposite, distal end which mounts a sealing member, and wherein the plunger assembly further includes a biasing member which is received about the shaft and which urges the sealing member into occluding relation relative to the primary passageway, and wherein force applied to the plunger assembly urges the sealing member into a displaced position relative to the valve body thereby permitting fluid flow.

13. A dental syringe as claimed in claim 12, and wherein the individual secondary passageways are disposed in fluid flowing relation relative to the respective connecting passageways, and wherein a substantially fluid impervious seal is received about each of the plunger portions.

14. A dental fluid delivery apparatus for delivering discrete fluids, comprising:

a housing having at least three fluid intake passageways, and an exhaust passageway, and wherein the fluid intake passageways are connected in fluid flowing relation relative to the exhaust passageway; and a plurality of selectively controllable valves borne by the housing and operable to selectively control fluid flow from the individual fluid intake passageways.

15. An apparatus as claimed in claim 14, and wherein the fluid intake passageways include first, second, and third fluid intake passageways, and wherein the first and second fluid intake passageways are serially connected in fluid discharging relation relative to the exhaust passageway, and the third passageway is individually connected in fluid discharging relation relative to the exhaust passageway.

16. An apparatus as claimed in claim 15, and wherein the individual valves each have a valve body which is received in the individual fluid intake passageways and are moveable along a given path of travel from a normally closed, fluid impeding position, to an open position which facilitates fluid flow.

17. An apparatus as claimed in claim 16, and wherein the housing further defines first and second connecting passageways which are individually connected in fluid flowing relation relative to the exhaust passageway, and wherein the first connecting passageway has first and second portions, and wherein the first portion connects, in fluid flowing relation, the first and second fluid intake passageways, and the second portion connects, in fluid flowing relation, the second fluid intake passageway to the exhaust passageway, and wherein the second connecting passageway couples the third fluid intake passageway to the exhaust passageway.

18. An apparatus as claimed in claim 17, and wherein the valve body includes a plunger and a shaft, and wherein the shaft has a proximal end which coacts with the plunger, and a distal end, and wherein the valve body has a primary passageway which is oriented along the longitudinal axis of the valve body and wherein the plunger is slidably received in the primary passageway, and wherein the valve body further defines a secondary passageway which is connected in fluid flowing relation relative to the primary passageway and the respective connecting passageways and which further is oriented in radially extending relation relative to the primary passageway.

19. An apparatus as claimed in claim 18, and wherein individual fluid seals are received about the valve body and the plunger respectively, and wherein a sealing member is borne on the distal end of the shaft and which is operable to occlude the primary passageway when the valve is disposed in the normally closed position, and is displaced a predetermined distance from the primary passageway when the valve is oriented in the open position, and wherein a biasing member is received about the shaft and urges the valve body into the normally closed position.

20. An apparatus as claimed in claim 14, and wherein the at least three intake passageways include a water intake passageway, a gas intake passageway and a medicament intake passageway.

21. An apparatus as claim in claim 14, and wherein the housing further defines first and second connecting passageways, and the first connecting passageway serially connects two of the three fluid intake passageways in fluid flowing relation relative to the exhaust passageway, and the second connecting passageway connects the remaining fluid intake passageway in fluid flowing relation relative to the exhaust passageway.

22. An apparatus as claim in claim 14, and further comprising a dispensing conduit connected to receive fluids from the exhaust passageway.

23. An apparatus as claim in claim 14, and wherein the individual valves each have a valve body which is received in the individual fluid intake passageways and moveable along a given path of travel from a normally closed, fluid impeding position, to an open position which facilitates fluid flow.

24. An apparatus for selectively delivering discrete fluids comprising:

a main body defining first, second, and third fluid intake passageways, first and second connecting passageways, and an exhaust passageway, and wherein the first connecting passageway connects, in fluid discharging relation, the first and second fluid intake passageways with the exhaust passageway, and the second connecting passageway connects, in fluid flowing relation, the third fluid intake passageway with the exhaust passageway;

a sleeve telescopingly received in sealing relation in each of the fluid intake passageways, each sleeve having an exterior facing, and an opposite, interior facing surface, and wherein the interior facing surface defines a primary passageway which is oriented along the longitudinal axis of the sleeve, and wherein a secondary passageway is formed in the sleeve and is disposed in fluid flowing relation relative to the primary passageway, and the respective connecting passageway;

a plunger movably borne by the sleeve and moveable along the primary passageway;

a shaft movably borne by the sleeve and having a distal end, the plunger coacting with the shaft, and moveable along a given path of travel from a first position, to a second position;

a biasing member received about the shaft and coacting with the sleeve, the biasing member urging the plunger and the shaft in the direction of the first position; and a sealing member borne on the distal end of each of the plungers and operable to occlude the primary passageway when the individual plungers are positioned in the first position, and is displaced a predetermined distance from the sleeve when the plunger is disposed in the second position thereby facilitating the flow of fluid from the respective intake passageways to the exhaust passageway.

25. Apparatus for delivering discrete fluids, comprising:

a housing having a plurality of fluid intake passageways, and an exhaust passageway, and wherein the fluid intake passageways are connected in fluid flowing relation relative to the exhaust passageway; and a plurality of selectively controllable valves borne by the housing and operable to selectively control fluid flow from the individual fluid intake passageways;

wherein the fluid intake passageways include first, second, and third fluid intake passageways, and wherein the first and second fluid intake passageways are serially connected in fluid discharging relation relative to the exhaust passageway, and the third passageway is individually connected in fluid discharging relation relative to the exhaust passageway.

26. An apparatus as claimed in claim 25, and wherein the individual valves each have a valve body which is received in the individual fluid intake passageways and are moveable along a given path of travel from a normally closed, fluid impeding position, to an open position which facilitates fluid flow.

27. An apparatus as claimed in claim 26, and wherein the housing further defines first and second connecting passageways which are individually connected in fluid flowing relation relative to the exhaust passageway, and wherein the first connecting passageway has first and second portions, and wherein the first portion connects, in fluid flowing relation, the first and second fluid intake passageways, and the second portion connects, in fluid flowing relation, the second fluid intake passageway to the exhaust passageway, and wherein the second connecting passageway couples the third fluid intake passageway to the exhaust passageway.

28. An apparatus as claimed in claim 27, and wherein the valve body includes a plunger and a shaft, and wherein the shaft has a proximal end which coacts with the plunger, and a distal end, and wherein the valve body has a primary passageway which is oriented along the longitudinal axis of the valve body and wherein the plunger is slidably received in the primary passageway, and wherein the valve body further defines a secondary passageway which is connected in fluid flowing relation relative to the primary passageway and the respective connecting passageways and which further is oriented in radially extending relation relative to the primary passageway.

29. An apparatus as claimed in claim 28, and wherein individual fluid seals are received about the valve body and the plunger respectively, and wherein a sealing member is borne on the distal end of the shaft and which is operable to occlude the primary passageway when the valve is disposed in the normally closed position, and is displaced a predetermined distance from the primary passageway when the valve is oriented in the open position, and wherein a biasing member is received about the shaft and urges the valve body into the normally closed position.

* * * * *